(12) United States Patent
Worboys et al.

(10) Patent No.: US 9,238,116 B2
(45) Date of Patent: Jan. 19, 2016

(54) CUSHION FOR A PATIENT INTERFACE (71) Applicant: ResMed Limited, Bella Vista, New South Wales (AU)

(72) Inventors: David John Worboys, Jilliby (AU); Susan Robyn Lynch, Maitland (AU)

(73) Assignee: RedMed Limited, Bella Vista (AU)

( * ) Notice: Subject to any disclaimer, the term of this patent is extended or adjusted under 35 U.S.C. 154(b) by 0 days.

(21) Appl. No.: 14/461,606

(22) Filed: Aug. 18, 2014

(65) Prior Publication Data
US 2014/0360507 A1    Dec. 11, 2014

Related U.S. Application Data

(63) Continuation of application No. 11/597,909, filed as application No. PCT/AU2005/000803 on Jun. 3, 2005, now Pat. No. 8,807,135.

(30) Foreign Application Priority Data

Jun. 3, 2004    (AU) ................ 2004902979

(51) Int. Cl.
*A61M 16/06*    (2006.01)
(52) U.S. Cl.
CPC ........... *A61M 16/0622* (2014.02); *A61M 16/06* (2013.01); *A61M 16/0605* (2014.02); *A61M 16/0616* (2014.02); *A61M 2016/0661* (2013.01)
(58) Field of Classification Search
CPC . A61M 16/00; A61M 16/06; A61M 16/0605; A61M 16/0611; A61M 16/0616; A61M 16/0622; A61M 2016/0661
See application file for complete search history.

(56) References Cited

U.S. PATENT DOCUMENTS

| 443,191 A | 12/1890 | Illing |
| 781,516 A | 1/1905 | Guthrie, Jr. |
| 1,081,745 A | 12/1913 | Johnston |
| 1,125,542 A | 1/1915 | Humphries |
| 1,192,186 A | 7/1916 | Greene |
| 1,229,050 A | 6/1917 | Donald |
| 1,282,527 A | 10/1918 | Bidonde |

(Continued)

FOREIGN PATENT DOCUMENTS

| AU | 199651130 | 10/1996 |
| AU | 2005100738 | 11/2005 |

(Continued)

OTHER PUBLICATIONS

Summons to Attend Oral Proceedings Pursuant to Rule 115(1) EPC issued Jul. 17, 2015, in a corresponding European Application No. 05746824.1 (4 pages).

(Continued)

*Primary Examiner* — Justine Yu
*Assistant Examiner* — Colin W Stuart
(74) *Attorney, Agent, or Firm* — Nixon & Vanderhye, P.C.

(57) ABSTRACT

A cushion for a patient interface includes an outer membrane providing a sealing structure adapted to form a seal with the patient's face in use and an underlying membrane generally spaced away from the outer membrane. The underlying membrane provides a support structure for the outer membrane. The outer membrane and the underlying membrane each have an inner edge which defines an aperture to receive the patient's nose in use. The underlying membrane is segmented along its inner edge.

20 Claims, 7 Drawing Sheets

(56) References Cited

U.S. PATENT DOCUMENTS

| | | |
|---|---|---|
| 1,362,766 A | 12/1920 | McGargill |
| 1,445,010 A | 2/1923 | Feinberg |
| 1,610,793 A | 12/1926 | Kaufman |
| 1,873,160 A | 8/1932 | Sturtevant |
| 2,353,643 A | 7/1944 | Bulbulian |
| 2,415,846 A | 2/1947 | Randall |
| 2,433,565 A | 12/1947 | Korman |
| 2,625,155 A | 1/1953 | Engelder |
| 2,706,983 A | 4/1955 | Matheson et al. |
| 2,931,356 A | 4/1960 | Schwarz |
| 3,013,556 A | 12/1961 | Galleher |
| 3,670,726 A | 6/1972 | Mahon et al. |
| 3,682,171 A | 8/1972 | Dali et al. |
| 3,739,774 A | 6/1973 | Gregory |
| 3,754,552 A | 8/1973 | King |
| 3,861,385 A | 1/1975 | Carden |
| 3,902,486 A | 9/1975 | Guichard |
| 3,905,361 A | 9/1975 | Hewson et al. |
| 3,938,614 A | 2/1976 | Ahs |
| 3,972,321 A | 8/1976 | Proctor |
| 4,006,744 A | 2/1977 | Steer |
| 4,142,527 A | 3/1979 | Garcia |
| 4,153,051 A | 5/1979 | Shippert |
| 4,156,426 A | 5/1979 | Gold |
| 4,248,218 A | 2/1981 | Fischer |
| 4,263,908 A | 4/1981 | Mizerak |
| 4,264,743 A | 4/1981 | Maruyama et al. |
| 4,267,845 A | 5/1981 | Robertson, Jr. et al. |
| 4,273,124 A | 6/1981 | Zimmerman |
| 4,312,359 A | 1/1982 | Olson |
| 4,367,735 A | 1/1983 | Dali |
| 4,367,816 A | 1/1983 | Wilkes |
| 4,406,283 A | 9/1983 | Bir |
| 4,414,973 A | 11/1983 | Matheson et al. |
| 4,422,456 A | 12/1983 | Tiep |
| 4,449,526 A | 5/1984 | Elam |
| 4,455,675 A | 6/1984 | Bose et al. |
| 4,493,614 A | 1/1985 | Chu et al. |
| 4,548,200 A | 10/1985 | Wapner |
| 4,549,542 A | 10/1985 | Chein |
| 4,572,323 A | 2/1986 | Randall |
| 4,587,967 A | 5/1986 | Chu et al. |
| 4,601,465 A | 7/1986 | Roy |
| 4,617,637 A | 10/1986 | Chu et al. |
| 4,630,604 A | 12/1986 | Montesi |
| 4,641,647 A | 2/1987 | Behan |
| 4,660,555 A | 4/1987 | Payton |
| 4,671,271 A | 6/1987 | Bishop et al. |
| 4,676,241 A | 6/1987 | Webb et al. |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| D293,613 S | 1/1988 | Wingler |
| 4,753,233 A | 6/1988 | Grimes |
| 4,767,411 A | 8/1988 | Edmunds |
| 4,774,946 A | 10/1988 | Ackerman et al. |
| 4,782,832 A | 11/1988 | Trimble et al. |
| 4,790,829 A | 12/1988 | Bowden et al. |
| 4,802,857 A | 2/1989 | Laughlin |
| 4,803,981 A | 2/1989 | Vickery |
| 4,811,730 A | 3/1989 | Milano |
| 4,830,138 A | 5/1989 | Palmaer et al. |
| 4,838,878 A | 6/1989 | Kalt et al. |
| 4,899,740 A | 2/1990 | Napolitano |
| 4,907,584 A | 3/1990 | McGinnis |
| 4,915,105 A | 4/1990 | Lee |
| 4,919,128 A | 4/1990 | Kopala et al. |
| 4,919,654 A | 4/1990 | Kalt |
| 4,944,310 A | 7/1990 | Sullivan |
| 4,945,907 A | 8/1990 | Tayebi |
| 4,951,664 A | 8/1990 | Niemeyer |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,989,599 A | 2/1991 | Carter |
| 4,996,983 A | 3/1991 | Amrhein |
| 5,000,173 A | 3/1991 | Zalkin et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,042,478 A | 8/1991 | Kopala et al. |
| 5,046,491 A | 9/1991 | Derrick |
| 5,074,297 A | 12/1991 | Venegas |
| 5,113,857 A | 5/1992 | Dickerman et al. |
| 5,117,818 A | 6/1992 | Palfy |
| 5,121,745 A | 6/1992 | Israel |
| 5,127,397 A | 7/1992 | Kohnke |
| 5,137,017 A | 8/1992 | Salter |
| 5,138,722 A | 8/1992 | Urella et al. |
| D333,015 S | 2/1993 | Farmer et al. |
| 5,188,101 A | 2/1993 | Tumolo |
| 5,207,665 A | 5/1993 | Davis et al. |
| 5,220,699 A | 6/1993 | Farris |
| 5,243,709 A | 9/1993 | Sheehan et al. |
| 5,243,971 A | 9/1993 | Sullivan |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,299,599 A | 4/1994 | Farmer et al. |
| 5,304,146 A | 4/1994 | Johnson et al. |
| 5,335,656 A | 8/1994 | Bowe et al. |
| 5,349,949 A | 9/1994 | Schegerin |
| 5,355,878 A | 10/1994 | Griffiths et al. |
| 5,355,893 A | 10/1994 | Mick et al. |
| 5,364,367 A | 11/1994 | Banks et al. |
| 5,372,130 A | 12/1994 | Stem et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,419,318 A | 5/1995 | Tayebi |
| 5,425,359 A | 6/1995 | Liou |
| 5,429,683 A | 7/1995 | Le Mitouard |
| 5,437,267 A | 8/1995 | Weinstein et al. |
| 5,441,046 A | 8/1995 | Starr et al. |
| 5,462,528 A | 10/1995 | Roewer |
| 5,477,852 A | 12/1995 | Landis et al. |
| 5,488,948 A | 2/1996 | Dubruille et al. |
| 5,509,409 A | 4/1996 | Weatherholt |
| 5,513,634 A | 5/1996 | Jackson |
| 5,513,635 A | 5/1996 | Bedi |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,540,223 A | 7/1996 | Starr et al. |
| 5,560,354 A | 10/1996 | Berthon-Jones et al. |
| 5,570,684 A | 11/1996 | Behr |
| 5,592,938 A | 1/1997 | Scarberry et al. |
| 5,623,923 A | 4/1997 | Bertheau et al. |
| 5,647,357 A | 7/1997 | Barnett et al. |
| 5,653,228 A | 8/1997 | Byrd |
| 5,655,527 A | 8/1997 | Scarberry et al. |
| 5,662,101 A | 9/1997 | Ogden et al. |
| 5,682,881 A | 11/1997 | Winthrop et al. |
| 5,704,345 A | 1/1998 | Berthon-Jones et al. |
| 5,707,342 A | 1/1998 | Tanaka |

(56) References Cited

U.S. PATENT DOCUMENTS

| | | |
|---|---|---|
| 5,724,965 A | 3/1998 | Handke et al. |
| 5,735,272 A | 4/1998 | Dillon et al. |
| 5,740,799 A | 4/1998 | Nielson |
| 5,752,511 A | 5/1998 | Simmons et al. |
| 5,794,619 A | 8/1998 | Edeiman et al. |
| 5,807,341 A | 9/1998 | Heim |
| 5,842,469 A | 12/1998 | Rapp et al. |
| 5,906,203 A | 5/1999 | Klockseth et al. |
| 5,918,598 A | 7/1999 | Belfer et al. |
| 5,921,239 A | 7/1999 | McCall et al. |
| 5,954,049 A | 9/1999 | Foley et al. |
| 5,975,079 A | 11/1999 | Hellings et al. |
| 6,019,101 A | 2/2000 | Cotner et al. |
| 6,026,811 A | 2/2000 | Settle |
| 6,044,844 A | 4/2000 | Kwok et al. |
| 6,082,360 A | 7/2000 | Rudolph et al. |
| 6,086,118 A | 7/2000 | McNaughton et al. |
| 6,095,996 A | 8/2000 | Steer et al. |
| 6,098,205 A | 8/2000 | Schwartz et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,193,914 B1 | 2/2001 | Harrison |
| 6,196,223 B1 | 3/2001 | Belfer et al. |
| 6,211,263 B1 | 4/2001 | Cinelli et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Haller et al. |
| 6,328,038 B1 | 12/2001 | Kessler et al. |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,358,279 B1 | 3/2002 | Tahi et al. |
| 6,374,826 B1 | 4/2002 | Gunaratnam et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,419,660 B1 | 7/2002 | Russo |
| 6,422,238 B1 | 7/2002 | Lithgow |
| 6,423,036 B1 | 7/2002 | Van Huizen |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,265 B2 | 1/2004 | Strickland et al. |
| 6,701,927 B2 | 3/2004 | Kwok et al. |
| 6,710,099 B2 | 3/2004 | Cinelli et al. |
| 6,766,800 B2 | 7/2004 | Chu et al. |
| 6,766,817 B2 | 7/2004 | da Silva |
| 6,776,162 B2 | 8/2004 | Wood |
| 6,776,163 B2 | 8/2004 | Dougill et al. |
| 6,789,543 B2 | 9/2004 | Cannon |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,860,270 B2 | 3/2005 | Sniadach |
| 6,895,965 B2 | 5/2005 | Scarberry et al. |
| 6,907,882 B2 | 6/2005 | Ging et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,011,090 B2 | 3/2006 | Drew et al. |
| 7,018,362 B2 | 3/2006 | Bierman et al. |
| 7,052,127 B2 | 5/2006 | Harrison |
| 7,066,586 B2 | 6/2006 | da Silva |
| 7,076,282 B2 | 7/2006 | Munro et al. |
| 7,080,645 B2 | 7/2006 | Genger et al. |
| 7,101,359 B2 | 9/2006 | Kline et al. |
| 7,107,989 B2 | 9/2006 | Frater et al. |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,191,781 B2 | 3/2007 | Wood |
| 7,207,328 B1 | 4/2007 | Altemus |
| 7,210,481 B1 | 5/2007 | Lovell et |
| 7,237,551 B2 | 7/2007 | Ho et al. |
| 7,243,723 B2 | 7/2007 | Surjaatmadja et al. |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,318,437 B2 | 1/2008 | Gunaratnam et al. |
| 7,523,754 B2 | 4/2009 | Lithgow |
| 7,658,189 B2 | 2/2010 | Davidson |
| 2001/0020474 A1 | 9/2001 | Hecker et al. |
| 2002/0005198 A1 | 1/2002 | Kwok et al. |
| 2002/0029780 A1 | 3/2002 | Frater et al. |
| 2002/0046755 A1 | 4/2002 | Devoss |
| 2002/0053347 A1 | 5/2002 | Ziaee |
| 2002/0066452 A1 | 6/2002 | Kessler et al. |
| 2002/0069872 A1 | 6/2002 | Gradon et al. |
| 2002/0096178 A1 | 7/2002 | Ziaee |
| 2002/0124849 A1 | 9/2002 | Billette De Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2002/0185134 A1 | 12/2002 | Bishop |
| 2003/0000526 A1 | 1/2003 | Goebel |
| 2003/0019495 A1 | 1/2003 | Palkon et al. |
| 2003/0019496 A1 | 1/2003 | Kopacko et al. |
| 2003/0079749 A1 | 5/2003 | Strickland et al. |
| 2003/0089373 A1 | 5/2003 | Gradon et al. |
| 2003/0111080 A1 | 6/2003 | Olsen et al. |
| 2003/0154980 A1 | 8/2003 | Berthon-Jones et al. |
| 2003/0168063 A1 | 9/2003 | Gambone et al. |
| 2003/0196656 A1 | 10/2003 | Moore et al. |
| 2003/0196658 A1 | 10/2003 | Ging et al. |

(56) References Cited

U.S. PATENT DOCUMENTS

| | | |
|---|---|---|
| 2004/0025882 A1 | 2/2004 | Madaus et al. |
| 2004/0025885 A1 | 2/2004 | Payne, Jr. |
| 2004/0045551 A1 | 3/2004 | Eaton et al. |
| 2004/0065328 A1 | 4/2004 | Amarasinghe et al. |
| 2004/0106891 A1 | 6/2004 | Langan et al. |
| 2004/0107968 A1 | 6/2004 | Griffiths |
| 2004/0111104 A1 | 6/2004 | Schein et al. |
| 2004/0112384 A1 | 6/2004 | Lithgow et al. |
| 2004/0118406 A1 | 6/2004 | Lithgow et al. |
| 2004/0127856 A1 | 7/2004 | Johnson |
| 2004/0211428 A1 | 10/2004 | Jones |
| 2004/0226564 A1 | 11/2004 | Persson |
| 2004/0226566 A1 | 11/2004 | Gunaratnam et al. |
| 2005/0011523 A1 | 1/2005 | Aylsworth et al. |
| 2005/0028822 A1 | 2/2005 | Sleeper et al. |
| 2005/0033247 A1 | 2/2005 | Thompson |
| 2005/0039757 A1 | 2/2005 | Wood |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0101933 A1 | 5/2005 | Marrs et al. |
| 2005/0150495 A1 | 7/2005 | Rittner et al. |
| 2005/0155604 A1 | 7/2005 | Ging et al. |
| 2005/0211252 A1 | 9/2005 | Lang et al. |
| 2005/0241644 A1 | 11/2005 | Gunaratnam et al. |
| 2005/0284481 A1 | 12/2005 | Meyer |
| 2006/0060200 A1 | 3/2006 | Ho et al. |
| 2006/0081250 A1 | 4/2006 | Bordewick et al. |
| 2006/0095008 A1 | 5/2006 | Lampropoulos et al. |
| 2006/0095009 A1 | 5/2006 | Lampropoulos et al. |
| 2006/0118117 A1 | 6/2006 | Berthon-Jones |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0237017 A1 | 10/2006 | Davidson et al. |
| 2006/0283461 A1 | 12/2006 | Lubke et al. |
| 2007/0023044 A1 | 2/2007 | Kwok et al. |
| 2007/0125387 A1 | 6/2007 | Zollinger et al. |
| 2007/0144525 A1 | 6/2007 | Davidson et al. |
| 2007/0186930 A1 | 8/2007 | Davidson et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0110469 A1 | 5/2008 | Weinberg |
| 2008/0200880 A1 | 8/2008 | Kyvik et al. |
| 2008/0257354 A1 | 10/2008 | Davidson et al. |
| 2009/0044808 A1 | 2/2009 | Guney et al. |
| 2010/0000534 A1 | 1/2010 | Kooij et al. |
| 2010/0018534 A1 | 1/2010 | Veliss et al. |

FOREIGN PATENT DOCUMENTS

| | | |
|---|---|---|
| DE | 185017 | 5/1907 |
| DE | 30 11 900 | 10/1980 |
| DE | 146 688 | 2/1981 |
| DE | 37 19 009 | 12/1988 |
| DE | 39 27 038 | 2/1991 |
| DE | 297 23 101 | 7/1998 |
| DE | 197 03 526 | 8/1998 |
| DE | 199 44 242 | 3/2001 |
| DE | 100 02 571 | 7/2001 |
| DE | 102 13 905 | 10/2002 |
| DE | 10 2004 055 433 | 11/2004 |
| EP | 0 288 937 | 11/1988 |
| EP | 0 427 474 | 5/1991 |
| EP | 0 466 960 | 1/1992 |
| EP | 0 303 090 | 4/1992 |
| EP | 0 658 356 | 6/1995 |
| EP | 0 776 679 | 6/1997 |
| EP | 1 099 452 | 5/2001 |
| EP | 1 258 266 | 11/2002 |
| EP | 1 481 702 | 12/2004 |
| FR | 2 720 280 | 12/1995 |
| GB | 532214 | 1/1941 |
| GB | 2 176 404 | 12/1986 |
| GB | 2 368 533 | 5/2002 |
| GB | 2 385 533 | 8/2003 |
| JP | 2000-515784 | 11/2000 |
| WO | WO 82/03548 | 10/1982 |
| WO | WO 87/01950 | 4/1987 |
| WO | WO 92/20392 | 11/1992 |
| WO | WO 92/20395 | 11/1992 |
| WO | WO 96/28207 | 9/1996 |
| WO | WO 98/04310 | 2/1998 |
| WO | WO 98/12965 | 4/1998 |
| WO | WO 98/23305 | 6/1998 |
| WO | WO 99/16327 | 4/1999 |
| WO | WO 99/25410 | 5/1999 |
| WO | WO 99/43375 | 9/1999 |
| WO | WO 99/61088 | 12/1999 |
| WO | WO 00/20072 | 4/2000 |
| WO | WO 00/38772 | 7/2000 |
| WO | WO 00/50121 | 8/2000 |
| WO | WO 00/06951 | 11/2000 |
| WO | WO 00/72905 | 12/2000 |
| WO | WO 00/74758 | 12/2000 |
| WO | WO 00/76568 | 12/2000 |
| WO | WO 00/78384 | 12/2000 |
| WO | WO 01/62326 | 8/2001 |
| WO | WO 01/95965 | 12/2001 |
| WO | WO 01/97892 | 12/2001 |
| WO | WO 01/97893 | 12/2001 |
| WO | WO 02/38221 | 5/2002 |
| WO | WO 02/45784 | 6/2002 |
| WO | WO 03/090827 | 11/2003 |
| WO | WO 03/105921 | 12/2003 |
| WO | WO 2004/022146 | 3/2004 |
| WO | WO 2004/041342 | 5/2004 |
| WO | WO 2004/073778 | 9/2004 |
| WO | WO 2004/078230 | 9/2004 |
| WO | WO 2005/053781 | 6/2005 |
| WO | WO 2005/063328 | 7/2005 |
| WO | WO 2005/086943 | 9/2005 |
| WO | WO 2005/099801 | 10/2005 |
| WO | WO 2005/110220 | 11/2005 |
| WO | WO 2005/118040 | 12/2005 |
| WO | PCT/AU2006/000031 | 1/2006 |
| WO | PCT/AU2006/000417 | 3/2006 |
| WO | PCT/AU2006/000770 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | PCT/AU2007/001936 | 12/2007 |
| WO | WO 2007/143772 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | WO 2009/108994 | 9/2009 |
| WO | WO 2009/109004 | 9/2009 |
| WO | WO 2010/028425 | 3/2010 |

OTHER PUBLICATIONS

U.S. Appl. No. 10/385,701, filed Aug. 2003, Berthon-Jones et al.
U.S. Appl. No. 10/533,928, filed Jul. 2005, Berthon-Jones.
U.S. Appl. No. 10/584,711, filed Dec. 2004, Davidson.
U.S. Appl. No. 10/655,622, filed Sep. 2003, Lithgow.
U.S. Appl. No. 10/781,929, filed Jan. 2008, Gunaratnam et al.

(56) References Cited

OTHER PUBLICATIONS

U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/309,696, filed Jan. 2009, Kwok et al.
U.S. Appl. No. 12/382,517, filed Mar. 2009, Lithgow.
U.S. Appl. No. 12/448,250, filed Jun. 2009, Veliss et al.
U.S. Appl. No. 12/461,448, filed Aug. 2009, Berthon-Jones.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/833,841, filed Jul. 2006, Veliss.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
"Ear Loop Face Mask," USPTO to assume before Applicant's filing date.
Adam J. Singer MD et al. "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com, USPTO to assume before Applicant's filing date.
ComfortLite™ 2, Respironics, http://comfortlite2.respironics.com, USPTO to assume before Applicant's filing date.
"If You Hate CPAP! You Need CPAP Pro®," www.cpappro.com, USPTO to assume before Applicant's filing date.
Webster's New World Dictionary, Third College Edition 1988, definition for engaged and flexible.
EP Supplementary Search Report issued in EP Application 03793493, dated Dec. 2, 2009.
European Search Report filed on Jul. 27, 2009 in EP Application No. 07784697.0.
European Search Report issued in EP 07845378.4, mailed Dec. 1, 2009.
Examination Report filed in New Zealand Application 539836, dated Aug. 25, 2005.
Examiner's Report No. 3 mailed Nov. 18, 2009 in New Zealand Application No. 2003275762.
Extended European Search Report dated Mar. 19, 2009 in European Application No. EP 08161249.
Extended European Search Report Mailed Sep. 3, 2009 in corresponding EP Application No. 09161984.1.
Extended European Search Report. Application No. EP 08154854, dated Nov. 27, 2008.
Fisher and Paykel Col.—Product Family—http://www.fphcare.com/osa/products.asp/, USPTO to assume before Applicant's filing date.
Hans Rudolph, Inc.—Mask Products—http://www.rudolphkc.com/products.php?category=MASKS, USPTO to assume before Applicant'filing date.
International Preliminary Report on Patentability for PCT/AU2004/001832, dated Jul. 3, 2006.
International Search Report filed in PCT/AU2006/000770, dated Aug. 3, 2006.
International Search Report for PCT/AU2007/001052, dated Oct. 9, 2007.
International Search Report for PCT/AU2007/001051, dated Nov. 5, 2007.
International Search Report for PCT/AU2004/001832, dated Mar. 24, 2005.
International Search Report for PCT/AU2007/001936, dated Mar. 4, 2008.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Office Action mailed Dec. 22, 2009 in European Appln. No. 04802133.1.
ResMed Co.—Mask Products—http://resmed.com/portal/site/ResMedUS/index.jsp? . . . , USPTO to assume before Applicant's filing date.
Respironics Co.—Mask Family—http://masksfamily.respironics.com/, USPTO to assume before Applicant's filing date.
Snapp Nasal Interface, Tiara Medical Systems, Inc.—http://www.tiaramed.com/asp_shops/shopdisplayproducts.asp?id=109 &cat=SNAPP%2A+Nasal+Interface, USPTO to assume before Applicant's filing date.
Subbu Venkatraman et al., "Review Skin Adhesives and Skin Adhesion 1. Transdermal Drug Delivery Systems," Biomaterials, vol. 19, 1998, pp. 1119-1136.
Supplementary European Search Report mailed Sep. 8, 2009 in European Appln. No. 04802133.1.
Supplementary European Search Report mailed Dec. 18, 2009 in European Application No. 03810331.3.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.
International Search Report PCT/AU2009/001144, dated Dec. 18, 2009.
Supplementary Search Report issued in European Appln. 05746824.1, dated Dec. 17, 2009.
International Search Report for PCT/AU2005/000803 mailed Jun. 30, 2005.
Office Action issued in Japanese Appln. No. 2007-513621 (Aug. 24, 2010) w/English translation.
Office Action issued in European Appln. No. 05746824.1 (Mar. 22, 2011).
Communication issued in a corresponding European Application No. 05 746 824.1 dated Sep. 4, 2012.

CUSHION FOR A PATIENT INTERFACE

CROSS-REFERENCE TO THE APPLICATIONS

This application is a continuation of U.S. patent application Ser. No. 11/597,909, filed Jul. 11, 2007, allowed, which is the U.S. National Phase of International Application PCT/AU2005/000803, filed Jun. 3, 2005, which designated the U.S. and claims the benefit of Australian Provisional Application No. 2004902979, filed Jun. 3, 2004. Each application mentioned above is hereby incorporated herein by reference in its entirety.

FIELD OF THE INVENTION

The invention relates to treatment of sleep disordered breathing. In particular, the invention relates to a cushion for a patient interface used for treatment of sleep disordered breathing.

BACKGROUND OF THE INVENTION

The use of nasal Continuous Positive Airway Pressure (nasal CPAP) to treat Sleep Disordered Breathing (SDB), for example Obstructive Sleep Apnea (OSA), was invented by Sullivan (See U.S. Pat. No. 4,944,310). Such treatment is typically accomplished using a source of air at positive pressure (e.g., a blower or flow generator) connected to a patient interface (e.g., a mask) via an air delivery conduit. To maintain a suitable pressure at the entrance to the patient's airways, it is necessary to provide a suitable seal between the patient interface and the patient's face. Early masks were glued to a patient's face every night. Today, however, the patient interface is usually held in position with headgear. Treatment is very successful in reducing SDB. However, gas pressurized in the range of 4-20 cmH$_2$O can be noisy and uncomfortable. Poorly fitting masks can provide an inadequate seal against leak. After wearing a mask all night, some patients can have pressure sores on their faces, especially in such sensitive regions as the nasal bridge. Thus, mask designers and manufacturers are constantly striving to provide patient interfaces which provide a comfortable seal.

A variety of masks are available, such as nasal, full-face, and nose and mouth masks.

Figure 1:
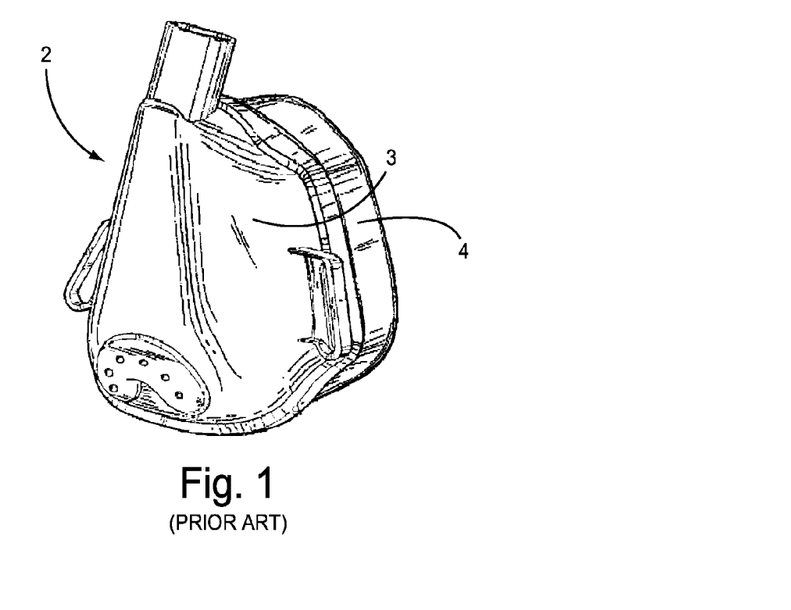
FIGS. 1-3 show various views of a prior art nasal MIRAGE® mask manufactured by ResMed.
Figure 2:
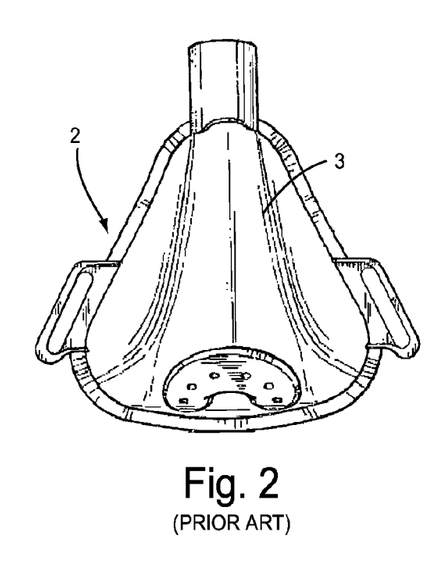
Figure 3:
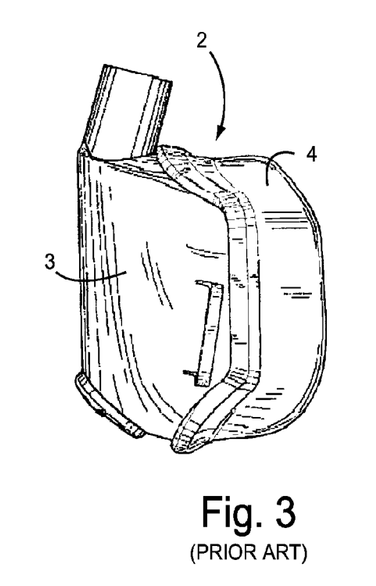

ResMed's MIRAGE® mask provided a significant improvement in masks for CPAP treatment. FIGS. 1-3 illustrate an embodiment of ResMed's MIRAGE® mask. It is available in both nasal and full-face versions. In the illustrated embodiment, the mask 2 includes (i) a rigid shell or frame 3 that defines a nose-receiving chamber, and (ii) a face-contacting cushion 4. The cushion 4 plays a role in improving the comfort and seal of the mask. For example, see U.S. Pat. Nos. 6,112,746; 6,357,441; 6,581,602 and 6,634,358. Other aspects of the mask, such as a forehead support and vent also play a role in the fit, comfort, and noise of a mask.

Figure 4:
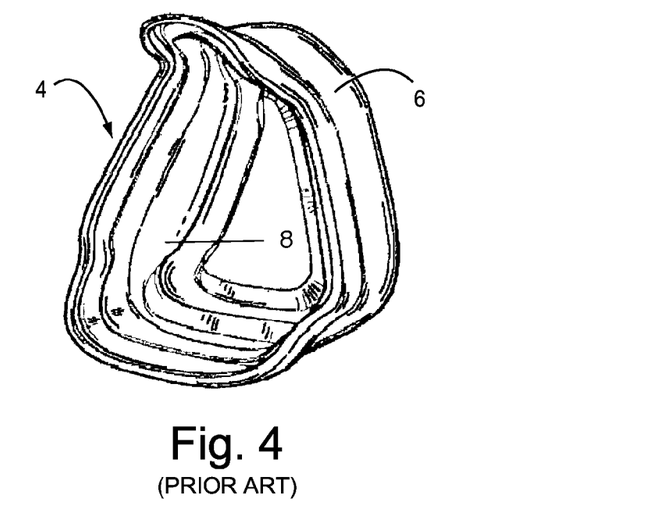
FIGS. 4-6 show various views of a prior art cushion for the nasal MIRAGE® mask shown in FIGS. 1-3.
Figure 5:
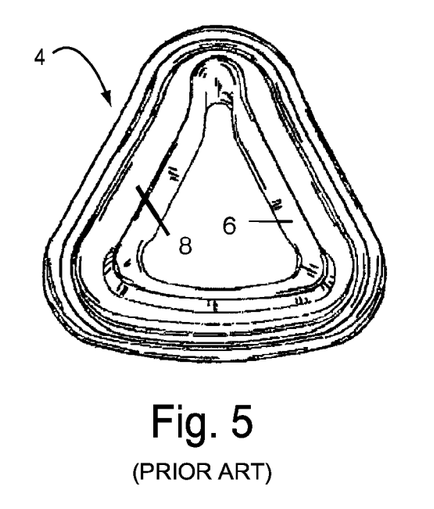
Figure 6:
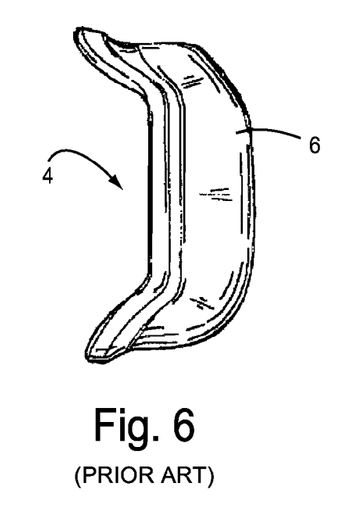

As shown in FIGS. 4-6, the cushion 4 of the MIRAGE® mask includes a dual membrane structure. As illustrated, the cushion 4 includes a thinner outer membrane 6 that is spaced away from a thicker inner or underlying membrane 8 at their inner edges.

The present invention is particularly directed towards a cushion with an improved inner or underlying membrane.

SUMMARY OF THE INVENTION

One aspect of the invention relates to a cushion for a respiratory mask having a segmented support structure.

Another aspect of the invention relates to a cushion for a respiratory mask having a dual membrane structure with an outer membrane and an underlying membrane divided into a series of finger portions.

Another aspect of the invention relates to a cushion for a patient interface. The cushion includes an outer membrane providing a sealing structure adapted to form a seal with the patient's face in use and an underlying membrane generally spaced away from the outer membrane. The underlying membrane provides a support structure for the outer membrane. The outer membrane and the underlying membrane each have an inner edge which defines an aperture to receive the patient's nose in use. The underlying membrane is segmented along its inner edge.

Still another aspect of the invention relates to a cushion adapted to be mounted on a frame of a patient interface for use with treatment of sleep disordered breathing. The cushion includes an outer membrane and an underlying membrane. The outer membrane is thinner than the underlying membrane and is generally spaced away from the underlying membrane and in use is adapted to contact a facial region of a patient. The underlying membrane has an inner edge defining an aperture and is divided along the edge to form a series of finger portions.

Yet another aspect of the invention relates to a cushion for a patient interface. The cushion includes a membrane and an underlying support structure provided along a side of the cushion to support the membrane. The underlying support structure is segmented.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

In a dual walled cushion, the outer wall (outer membrane) can define a sealing structure and the inner wall (inner membrane) can define a support structure. A seal can form when a patient's face is lightly pressed against the outer membrane. However, the outer membrane will easily flex upon contact with the patient's face. The inner membrane is generally thicker and more rigid than the outer membrane. When a patient's face presses against the outer membrane, the gap between the two membranes reduces. At a larger contact force, there may be no gap between the two membranes. With a yet higher contact force, the inner membrane will also begin to flex. In response to a contact force from a patient's face to the cushion, the cushion will provide a reaction force from the cushion to the patient's face. The size and direction of the resultant reaction force in a particular region will depend upon the face and cushion properties in that region.

Figure 7:
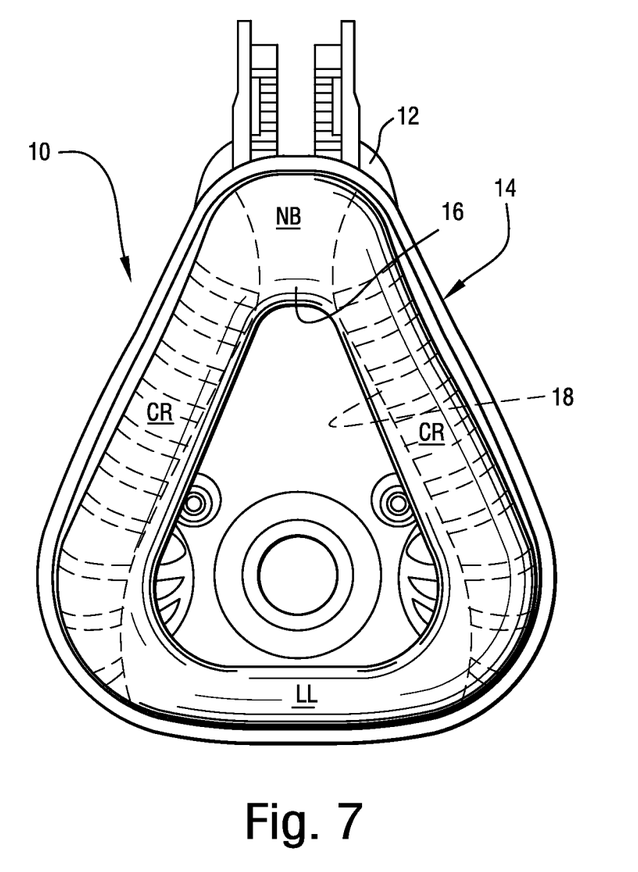
FIG. 7 shows a rear view of a full-face mask according to an embodiment of the invention.

FIG. 7 illustrates a patient interface in the form of a full-face mask 10 including a cushion 14 in accordance with an embodiment of the invention. The cushion 14 is structured to be attached to a substantially rigid frame 12 associated with an air delivery tube. The cushion 14 may be removably or permanently attached to the frame 12 in any suitable manner.

As illustrated, the cushion 14 has a thin outer membrane 16 and a thicker underlying membrane 18 generally spaced away from the outer membrane 16. The outer membrane 16 provides a sealing structure to form a seal with the patient's face, and the underlying membrane 18 (also referred to as an underlying support) provides a support structure for the outer membrane 16. Both the outer and underlying membranes 16, 18 have an inner edge which defines an aperture through which a nose passes in use.

In the illustrated embodiment, the outer membrane 16 forms a seal with a nasal bridge region NB, cheek regions CR, and a lower lip region LL of the patient's face. Also, the cushion 14 has a double-walled construction, i.e., outer membrane 16 and underlying membrane 18, in the cheek regions CR and a single-walled construction, i.e., outer membrane 16, in the nasal bridge and lower lip regions NB, LL. The single wall construction at the top and bottom of the cushion 14 allows flexibility to accommodate a wide range of patients. However, the cushion 14 may have any other suitable construction, e.g., single walled, triple walled or more walled construction, in any suitable region of the cushion 14.

Figure 8:
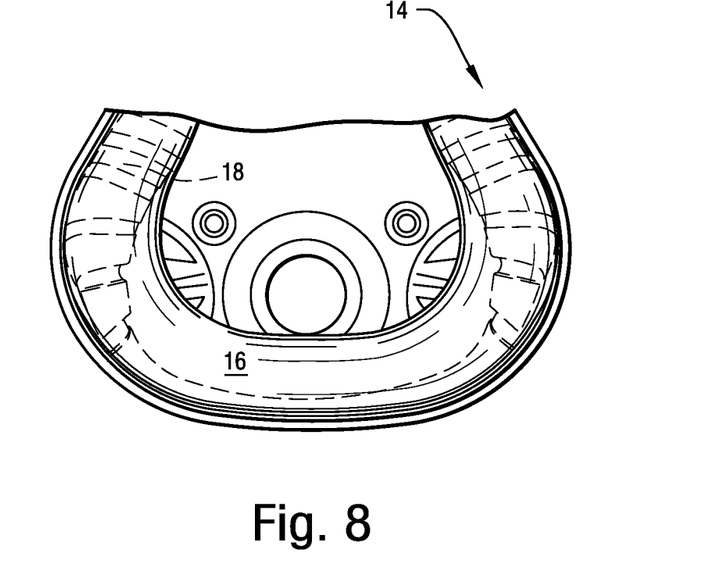
FIG. 8 shows a bottom detail view of the mask of FIG. 7.
Figure 9:
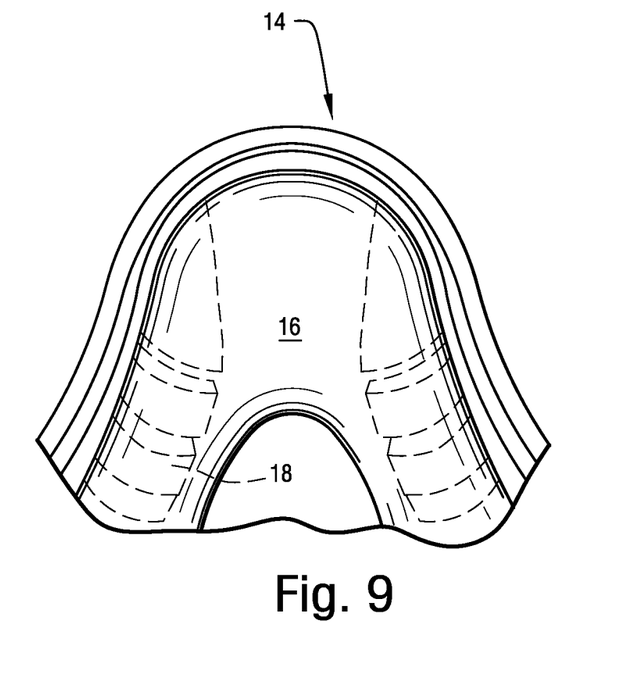
FIG. 9 shows a top detail view of the mask of FIG. 7.
Figure 10:
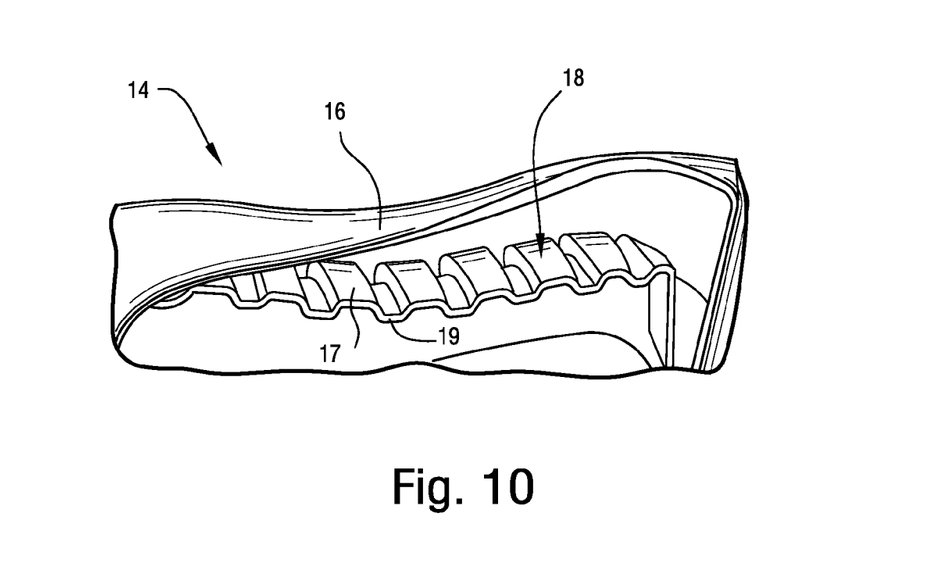
FIG. 10 shows a side detail view of the mask of FIG. 7.

As best shown in FIGS. 8-10, the underlying membrane 18 is segmented along its inner edge. In the preferred embodiment, the line of segmentation is generally perpendicular to the edge, however in other forms it may not be. The segmentation provides a set of finger portions 17 interconnected by webbing 19.

In the illustrated embodiment, the underlying membrane 18 is a continuous material with the webbing 19 fainted in a different plane than the finger portions 17. However, the webbing 19 may have other suitable configurations. For example, the webbing 19 may be in the form of one or more connecting members than extend between and interconnect at least adjacent portions of adjacent finger portions 17. The one or more connecting members may be positioned between intermediate portions of adjacent finger portions 17 so that tips of the finger portions are exposed. Alternatively, the one or more connecting members may be positioned between end portions of adjacent finger portions 17 so that the connecting members are substantially continuous with tips of the finger portions. Other arrangements are also possible to reinforce and interconnect the finger portions 17.

Each finger portion 17 is generally independently flexible. That is, a local force on one group of finger portions 17 will not directly transfer to an adjacent group. Thus, flexion of the cushion 14 in one region will not necessarily cause flexion of the cushion 14 in an adjacent region to the same extent as the prior art. This arrangement provides independent suspension of different facial regions in contact with the cushion 14, and allows the cushion 14 to conform more closely to the patient's face.

Furthermore, in the nasal bridge region NB and lower lip/chin region LL (see FIG. 7), the underlying membrane 18 is progressively or completely shortened. Reducing or eliminating the underlying membrane 18 in these regions of the cushion 14 means the outer membrane 16 can "give" more when a face contacts it. This arrangement can improve comfort in these sensitive regions.

In one form, the cushion 14 is mechanically equivalent to a series of composite springs placed around a nose receiving aperture of the frame. The composite spring has mechanical properties derived from the combination of the sealing and support structures, which in one form are two membranes. The properties of the "springs equivalents" in the nasal bridge and lower lip/chin regions NB, LL can be and preferably are different than those in the cheek regions CR (see FIG. 7), in this embodiment.

Figure 11:
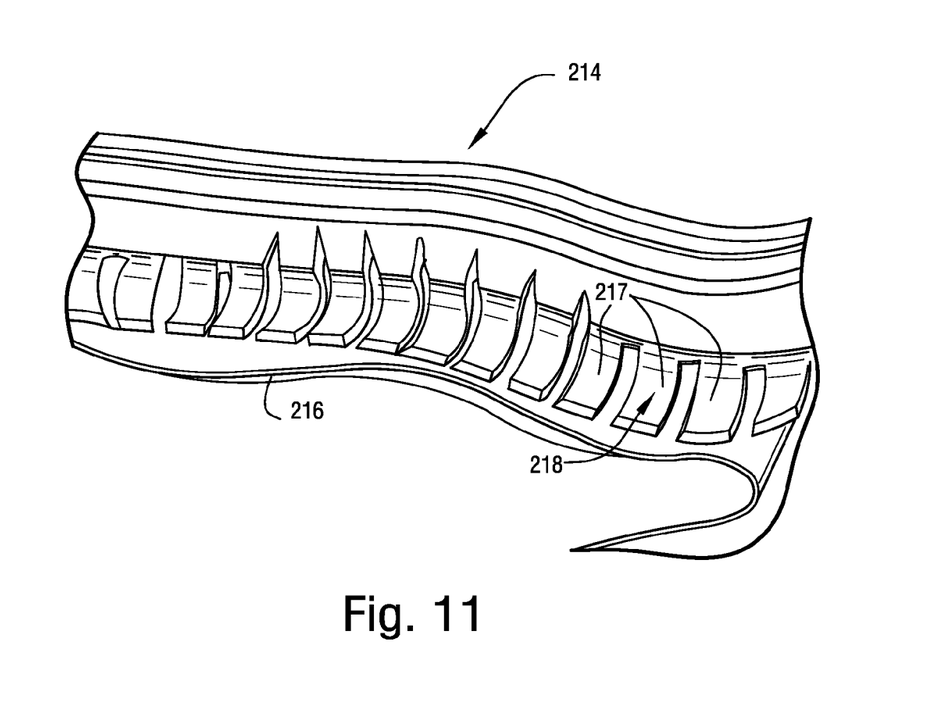
FIG. 11 shows an enlarged perspective view of a cushion according to an alternative embodiment of the invention.
Figure 12:
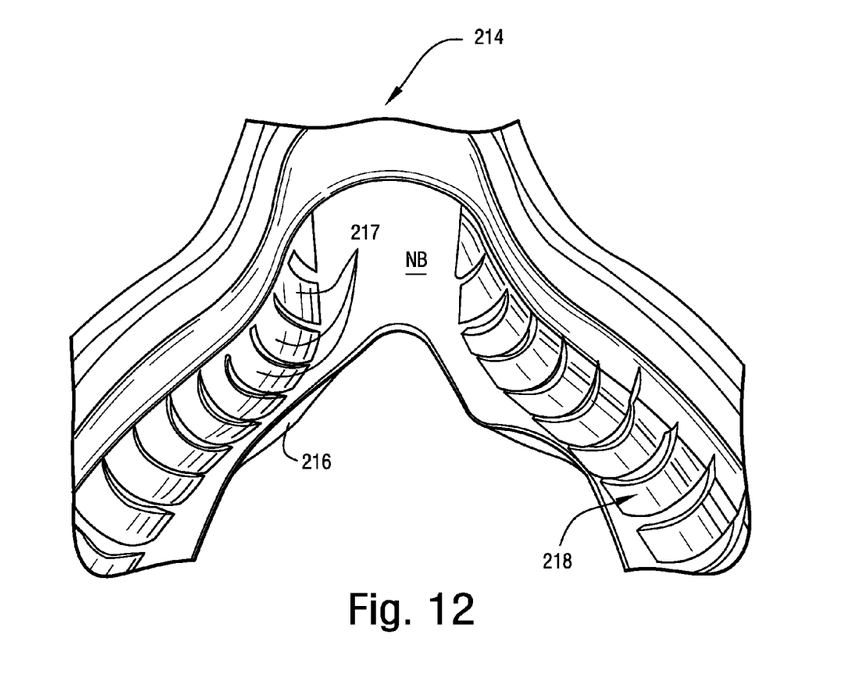
FIG. 12 shows a top detail view of the cushion of FIG. 11.

FIGS. 11 and 12 illustrate a cushion 214 according to another embodiment of the invention. In this embodiment, the cushion 214 includes an outer membrane 216 and underlying membrane 218 segmented into a set of finger portions 217. In contrast the cushion 14, there is no webbing between the finger portions 217 of the cushion 214. Like the previous embodiment, the fingers 217 are progressively shorter in a nasal bridge region NB of the cushion 214 (see FIG. 12). In an embodiment, the depth and/or length of the slot between adjacent finger portions 217 may be selectively adjusted to adjust the flexibility of selected finger portions 217. The depth and/or length of the slot may be adjusted so that the finger portions 217 are more flexible in certain regions of the patient's face.

In the two above-described embodiments, the cushion 14, 214 is constructed from silicone. However, other materials may be used, such as gel and foam. FIGS. 11-12 show a MIRAGE® full face cushion modified in accordance with the invention.

Figure 13:
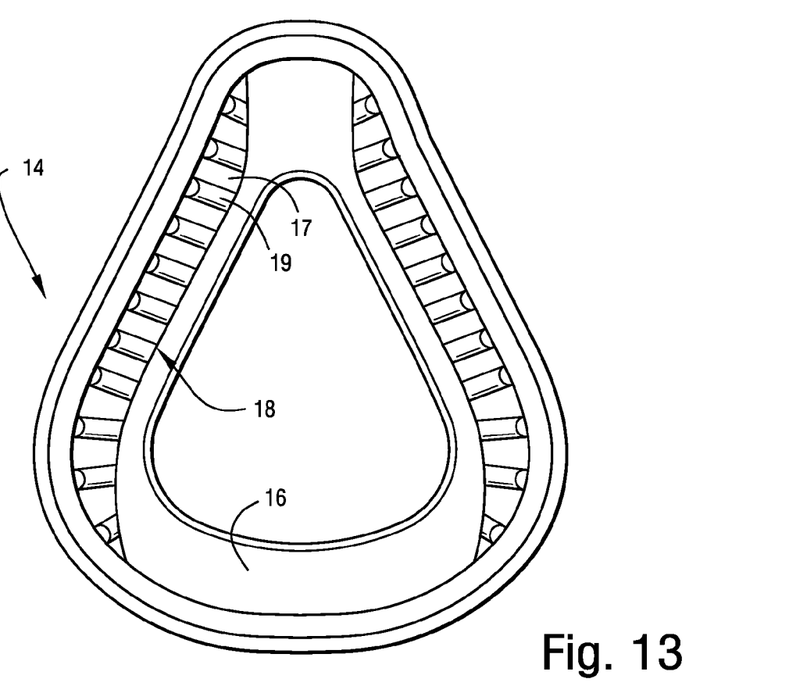
FIGS. 13-14 show rear and side views of a cushion of the mask of FIG. 7, and the cushion opening has not been cut from molding.
Figure 14:
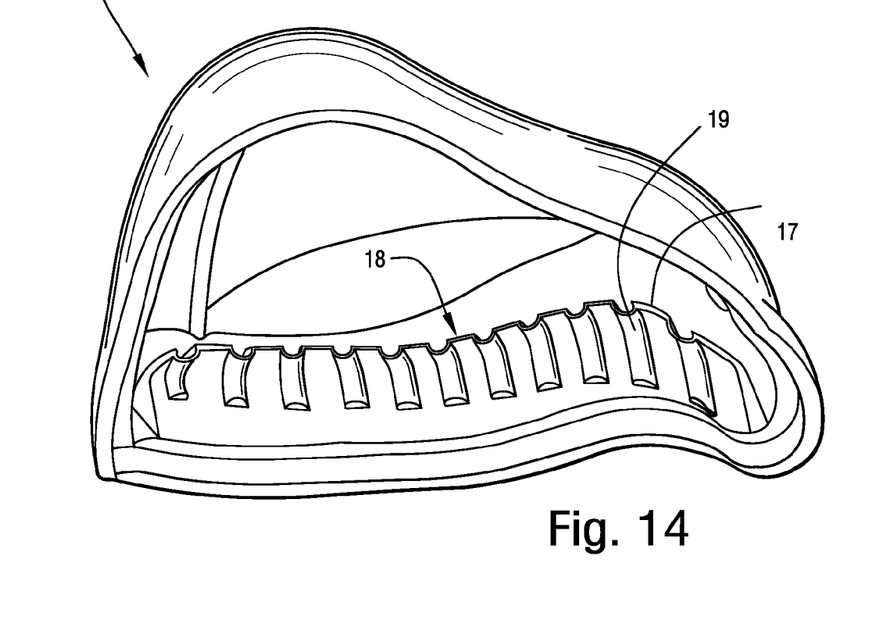

Other views of the segmented cushion 14 with webbing are shown in FIGS. 13 and 14. In these views, the cushion opening has not been cut from molding.

The cushion 14, 214 described above has several advantages. For example, the cushion 14, 214 is structured to alleviate the pressure of the cushion on the patient's face. Also, the cushion 14, 214 is structured to conform and seal to different patient facial profiles. Further, the cushion 14, 214 is locally compliant.

Although our invention has been described with reference to particular embodiments, it is to be understood that these embodiments are merely illustrative of the application of the principles of the invention. Numerous modifications may be made therein and other arrangements may be devised without departing from the spirit and scope of the invention. For example, whilst in a preferred embodiment, the cushion includes two membranes, it is also applicable to cushions with one, three or more membranes. Furthermore, the principles of the invention may be applied to a variety of different patient interfaces, such as nasal mask, nose and mouth masks, full-face masks, nasal prongs and nasal cushions. In different cushions, the role of sealing and support structures can be combined into one physical structure. Fingers may be shaped or adjusted to suit the needs of individual patients.

Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A cushion for a patient interface, the cushion including a nasal bridge region, a pair of cheek regions and a lower lip region, the cushion comprising:
   an outer membrane providing a sealing structure adapted to form a seal with a patient's face when the cushion is worn; and
   an underlying membrane spaced away from the outer membrane, the underlying membrane providing a support structure for the outer membrane,
   wherein the outer membrane and the underlying membrane each have an inner edge which defines an aperture to receive the patient's nose when the cushion is worn, and the underlying membrane is segmented along its inner edge to provide a plurality of finger portions and a plurality of slots separating the plurality of finger portions,
   wherein each slot is disposed between a respective two adjacent finger portions, each slot having a depth measured from the inner edge of the underlying membrane, and slots in the nasal bridge region of the cushion have depths that are different than depths of slots in the pair of cheek regions and/or the lower lip region of the cushion to vary flexibility of the plurality of finger portions around a cushion perimeter, and
   wherein the depth of each slot is measured from the inner edge of the underlying membrane to an end of a through-hole in the underlying membrane formed by the respective slot.

2. A cushion according to claim 1, wherein the segmented underlying membrane is structured to provide local compliance.

3. A cushion according to claim 1, wherein the segmented underlying membrane is structured to provide relative movement along its inner edge in conformance with different facial regions in contact with the cushion when the cushion is worn.

4. A cushion according to claim 1, wherein the underlying membrane is thicker than the outer membrane.

5. A cushion according to claim 1, wherein the outer membrane is configured to form a seal with a nasal bridge region, a pair of cheek regions, and a lower lip region of the patient's face when the cushion is worn.

6. A cushion according to claim 1, wherein the underlying membrane includes a line of segmentation that extends substantially perpendicular to its inner edge.

7. A cushion according to claim 1, wherein the underlying membrane is reduced or eliminated in at least one of the nasal bridge region and the lower lip region of the cushion.

8. A cushion according to claim 1, wherein the plurality of finger portions are independently flexible to allow the cushion to conform to different patient facial profiles.

9. A cushion according to claim 1, wherein the inner edge of the outer membrane and the inner edge of the underlying membrane both curve inwardly from a side wall in a cantilever manner towards a nose receiving cavity of the cushion.

10. A patient interface comprising:
    a frame; and
    a cushion according to claim 1.

11. A cushion adapted to be mounted on a frame of a patient interface for use with treatment of sleep disordered breathing, the cushion including a nasal bridge region, a pair of cheek regions and a lower lip region, the cushion comprising:
    an outer membrane; and
    an underlying membrane,
    the outer membrane being thinner than the underlying membrane and being spaced away from the underlying membrane and when the cushion is worn being adapted to contact a facial region of a patient,
    the underlying membrane having an inner edge defining an aperture and being divided along the inner edge to form a plurality of flexible finger portions and a plurality of slots separating the plurality of finger portions,
    wherein each slot is disposed between a respective two adjacent finger portions, each slot having a length measured from the inner edge of the underlying membrane, and the lengths of a first group of slots of the plurality of slots being different than the lengths of a second group of slots of the plurality of slots to vary flexibility of the plurality of finger portions around a cushion perimeter, and
    wherein the length of each slot is measured from the inner edge of the underlying membrane to an end of a through-hole in the underlying membrane formed by the respective slot.

12. A cushion according to claim 11, wherein the underlying membrane includes a line of segmentation that extends substantially perpendicular to the inner edge.

13. A cushion according to claim 11, wherein the underlying membrane is reduced or eliminated in at least one of the nasal bridge region and the lower lip region of the cushion.

14. A cushion according to claim 11, wherein the underlying membrane is structured to provide relative movement along its inner edge in conformance with different facial regions in contact with the cushion when the cushion is worn.

15. A cushion according to claim 11, wherein the outer membrane forms a seal with a nasal bridge region, a pair of cheek regions, and a lower lip region of the patient's face when the cushion is worn.

16. A cushion according to claim 11, wherein the underlying membrane is provided only in the pair of cheek regions of the cushion.

17. A cushion for a patient interface, the cushion including a nasal bridge region, a pair of cheek regions and a lower lip region, the cushion comprising:
    a membrane; and
    an underlying support structure provided along a side of the cushion to support the membrane, the underlying support structure being segmented and configured to conform to a patient's face when the cushion is worn,
    wherein the segmented underlying support structure provides a series of alternating finger portions and slots along the cushion perimeter, and slots along a cushion perimeter,
    wherein depths of at least two of the slots are different to vary flexibility of the series of finger portions, and
    wherein the underlying support structure has an inner edge which defines an aperture to receive the patient's nose when the cushion is worn, each depth being measured from the inner edge to an end of a through-hole in the underlying support structure formed by the respective slot.

18. A cushion according to claim 17, wherein the underlying support structure is reduced or eliminated in at least one of the nasal bridge region and the lower lip region of the cushion.

19. A cushion according to claim 17, wherein the underlying support structure is structured to provide relative movement along its inner edge in conformance with different facial regions in contact with the cushion when the cushion is worn.

20. A cushion according to claim 17, wherein the underlying support structure is provided only in the pair of cheek regions of the cushion.

* * * * *